(12) United States Patent
Alving et al.

(10) Patent No.: US 10,788,595 B2
(45) Date of Patent: Sep. 29, 2020

(54) DRIVING OF AN X-RAY DETECTOR TO COMPENSATE FOR CROSS SCATTER IN AN X-RAY IMAGING APPARATUS

(71) Applicant: KONINKLIJKE PHILIPS N.V., Eindhoven (NL)

(72) Inventors: Peter Lex Alving, Mierlo (NL); Heidrun Steinhauser, Einndhoven (NL); Herman Stegehuis, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 227 days.

(21) Appl. No.: 16/078,811

(22) PCT Filed: Feb. 21, 2017

(86) PCT No.: PCT/EP2017/053951
§ 371 (c)(1),
(2) Date: Aug. 22, 2018

(87) PCT Pub. No.: WO2017/144474
PCT Pub. Date: Aug. 31, 2017

(65) Prior Publication Data
US 2019/0056517 A1    Feb. 21, 2019

(30) Foreign Application Priority Data
Feb. 23, 2016   (EP) .................................. 16156997

(51) Int. Cl.
*G01T 1/29* (2006.01)
*A61B 6/00* (2006.01)
(Continued)

(52) U.S. Cl.
CPC .......... *G01T 1/2928* (2013.01); *A61B 6/4233* (2013.01); *G01N 23/04* (2013.01);
(Continued)

(58) Field of Classification Search
CPC ......... G01T 1/2928; G01T 1/244; G01T 1/20; G01T 1/2018; G01T 1/247;
(Continued)

(56) References Cited

U.S. PATENT DOCUMENTS 3,669,521 A * 6/1972 Tait ...................... G11C 13/042
                                                          365/125
5,432,334 A    7/1995 Nelson
(Continued)

FOREIGN PATENT DOCUMENTS

DE    19524858 A1    1/1997
EP     1014683 A2    6/2000
EP     2364026 A2    9/2011

*Primary Examiner* — David P Porta
*Assistant Examiner* — Gisselle M Gutierrez
(74) *Attorney, Agent, or Firm* — Larry Liberchuk

(57) ABSTRACT

The present invention relates to an apparatus for imaging an object. It is described to receive (110) by at least a portion of first pixels of a first area (A, A1, A2, A3, A4, A5, A6, A7, A8) of an X-ray detector (20) first radiation emitted by at least one X-ray source (30). The X-ray detector is configured such that X-ray radiation received by a pixel leads to the generation of signal in that pixel. A plurality of first signals representative of corresponding signals on the plurality of first pixels are stored (120) in at least one first plurality of storage nodes associated with the first area. Second radiation emitted by the at least one X-ray source (30) is received (150) by at least a portion of second pixels of a second area (B, B1, B2, B3, B4, B5, B6, B7, B8; C) of the X-ray detector. A plurality of second signals representative of corresponding signals on the plurality of second pixels are stored (190) in at least one second plurality of storage nodes associated with the second area.

11 Claims, 9 Drawing Sheets

(51) Int. Cl.
*G01T 1/20* (2006.01)
*G01T 1/24* (2006.01)
*G01N 23/04* (2018.01)
*G01N 23/083* (2018.01)
*H04N 5/32* (2006.01)
*H04N 5/3745* (2011.01)

(52) U.S. Cl.
CPC ............. *G01N 23/083* (2013.01); *G01T 1/20* (2013.01); *G01T 1/2018* (2013.01); *G01T 1/244* (2013.01); *G01T 1/247* (2013.01); *H04N 5/32* (2013.01); *H04N 5/37452* (2013.01)

(58) Field of Classification Search
CPC .... H04N 5/37452; H04N 5/32; A61B 6/4233; G01N 23/04; G01N 23/083; G01N 23/0344
USPC ...................................................... 378/98.12
See application file for complete search history.

(56) References Cited

U.S. PATENT DOCUMENTS

| | | |
|---|---|---|
| 6,894,283 B1 | 5/2005 | Busse |
| 7,119,341 B2 | 10/2006 | Petrick |
| 7,831,109 B2 | 11/2010 | Maack |
| 9,869,774 B2 * | 1/2018 | Dowaki ................. H04N 5/361 |
| 2005/0018065 A1 | 1/2005 | Tashiro |
| 2005/0157841 A1 | 7/2005 | Chopra |
| 2007/0051976 A1 | 3/2007 | Moody |
| 2008/0232549 A1 * | 9/2008 | Poorter ................. A61B 6/4035 378/98.9 |
| 2009/0194672 A1 | 8/2009 | Tredwell |
| 2009/0244337 A1 | 10/2009 | Kume |
| 2009/0279659 A1 | 11/2009 | David |
| 2013/0240712 A1 | 9/2013 | Takenaka |
| 2016/0134818 A1 * | 5/2016 | Iwashita ................. H04N 5/361 348/162 |

* cited by examiner conventional (a-Si) detector detector with n x m block FT

One big group

Two groups

Nine groups

Centered overlapping groups

Overlapping groups

Non square detector

DRIVING OF AN X-RAY DETECTOR TO COMPENSATE FOR CROSS SCATTER IN AN X-RAY IMAGING APPARATUS

FIELD OF THE INVENTION

The present invention relates to an apparatus for imaging an object, to an X-ray detector for imaging an object, and to a method for imaging an object, as well as to a computer program element and a computer readable medium.

BACKGROUND OF THE INVENTION

To minimize motion artifacts in imaging, beams from different viewing directions should be acquired as closely in time as possible. Simultaneous exposure can give unacceptable cross-scatter. Detector read-out of a 1st exposure should be finished before a 2nd exposure can occur. This is because the cross-scatter from the 2nd exposure is added to the signal charge of the 1st exposure being read-out. Non-simultaneous (or subsequent exposures) on the other hand, can lead to unacceptable motion artifacts. In a conventional detector, with 4 simultaneous beams, an overall read out time is equal to the time to read out the detector added to the exposure pulse duration and suffers from high cross-scatter. On the other hand, a sequential read out of the 4 beams requires an overall readout equal to four times that for the simultaneous case, and motion artifacts can be unacceptable.

US2005/157841A describes an imaging system for generating an image of a planar segment of an object. The imaging system includes an x-ray source, a planar detector, and a controller. The x-ray source generates x-rays from first and second source points, the x-rays from the first and second source points passing through the object. The planar detector includes a plurality of photodetectors covered by a layer of scintillation material that converts x-rays into visible light, the planar detector is positioned to receive x-rays from the first and second source points after the x-rays have passed through the object. The controller selects which of the source points generates the x-rays at any given time. The controller reads a first image formed by x-rays from the first source point and stored in a first portion of the planar detector while a second portion of the photodetectors measures x-rays from the second source point.

US2013/240712A describes a radiation imaging apparatus, comprising an imaging unit in which a plurality of pixels are arranged to form a plurality of rows and a plurality of columns, and a control unit configured to control the imaging unit so as to perform reset operation for initializing each of the plurality of pixels repeatedly, and readout operation, after the reset operation, for reading out a signal from each of the plurality of pixels sequentially, wherein one cycle length of the reset operation is shorter than a period of time required for the readout operation, and a pulse width of a signal supplied to each of the plurality of pixels in the reset operation is shorter than a pulse width of a signal supplied to each of the plurality of pixels in the readout operation.

U.S. Pat. No. 5,432,334A describes that a radiation imaging method and system for use in various imaging techniques includes a source of radiation at first and second wavelengths. A first radiation target array receives the radiation from the first wavelength at first spacial locations to produce an array of output signals at locations within the first radiation target array related to the magnitude of the radiation at each of the first spacial locations. A second radiation target array receives the radiation at the second wavelength at second spacial locations to produce an array of output signals at locations within the second radiation target array related to the magnitude of the radiation at each of the second spacial locations. The first and second outputs are combined to produce combined image signals that has increased contrast from that which would be produced by either the first or the second output alone. In a preferred embodiment, the first and second radiation target arrays comprise amorphous silicon arrays in which sensor data from the first and second radiation targets is synchronously clocked from the array.

US2005/018065A describes an image pickup apparatus comprising an image pickup element having pixels arranged in a two-dimensional state, each pixel having a photoelectric conversion portion, a first holding portion for holding a photoelectric conversion signal generated in the photoelectric conversion portion and a second holding portion for holding a noise signal generated in the pixel.

US2009/244337A describes a solid-state imaging apparatus including: a pixel section where a plurality of pixels each containing a photoelectric conversion device are formed into an array; a retaining circuit for retaining one or the other of a reset signal and a light signal of the signals from the pixel; and an AD converter, the AD converter includes: a delay circuit having two input signal terminals to one of the input signal terminals of which the signal retained at the retaining circuit is inputted and to the other one of the input signal terminal of which the other signal not retained at the retaining circuit is inputted, said delay circuit having delay devices connected into a multiple of stages for giving to a running pulse a delay amount corresponding to the extent of a difference between the signals inputted to said one and the other input signal terminals; and an encoder for sampling and encoding a running position of the pulse at every predetermined timing to generate a digital value corresponding to the difference between the input signals.

SUMMARY OF THE INVENTION

It would be advantageous to have improved apparatus for imaging an object, such as for 4D imaging.

The object of the present invention is solved with the subject matter of the independent claims, wherein further embodiments are incorporated in the dependent claims. It should be noted that the following described aspects of the invention apply also for the apparatus for imaging an object, X-ray detector for imaging an object, the method for imaging an object, and for the computer program element and the computer readable medium.

According to a first aspect, there is provided an apparatus for imaging an object, comprising:

an X-ray detector; and at least one X-ray source.

The at least one X-ray source is configured to be positioned relative to the X-ray detector such that at least a part of the region between the at least one X-ray source and the X-ray detector is an examination region for accommodating an object. The X-ray detector comprises a plurality of X-ray radiation detecting areas. The plurality of X-ray detecting areas comprises a first area comprising a plurality of first pixels and a second area comprising a plurality of second pixels. A first radiation emitted by the at least one X-ray source is receivable by at least a portion of the first pixels, and a second radiation emitted by the at least one X-ray source is receivable by at least a portion of the second pixels. The X-ray detector is configured such that the X-ray radiation received by a pixel leads to the generation of signal in that pixel. The X-ray detector comprises at least one first plurality of storage nodes associated with the first area and at least one second plurality of storage nodes associated with the second area. The at least one first plurality of storage nodes is configured to store a plurality of first signals representative of corresponding signals on the plurality of first pixels and the at least one second plurality of storage nodes is configured to store a plurality of second signals representative of corresponding signals on the plurality of second pixels. The at least one second plurality of storage nodes is configured to store the plurality of second signals after the at least one first plurality of storage nodes is configured to store the plurality of first signals.

In other words, the apparatus can be used for 4D imaging an object. Here, a first radiation means a pulse of radiation that can be emitted by the at least one X-ray source, with the second radiation meaning a pulse of radiation that can be emitted by the at least one X-ray source, that is different to the first radiation. In an example, the first and second radiations are emitted by different X-ray sources. In an example, the first and second radiations are emitted by the same X-ray source, which has an extended emitting area, with apertures and/or shutters used. In an example, the first and second radiations are emitted by the same X-ray source that is at one spatial position for emission of the first radiation and is at a second spatial position for emission of the second radiation (in other words, the X-ray source can be moveable in this example).

In this manner, a single detector can provide the advantages that would be required through the use of two detectors or more than two detectors, however the manner in which signals are handled provides this functionality in a single detector with the added advantage that no dead area exists between the detectors with the added advantages of reduced cost, size and power consumption. By having only one detector, system integration can be improved.

In this way, cross scatter can be reduced in a system operating with 2 X-ray beams simultaneously irradiating one half of a detector followed by 2 X-ray beams simultaneously irradiating a second half of the detector, and the cycle time of operation is equal to the read-out time. In this manner, the cycle time is now dominated by either two exposure times or one readout time, whichever is the longest in contrast to the sum of two readouts and two exposures times. In this way, cross scatter can further be reduced in a system operating with one X-ray beam irradiating a first part of one half of a detector, followed by a second X-ray beam irradiating the second part of that first half of the detector, followed by a third X-ray beam irradiating a first part of a second half of the detector, followed by a fourth X-ray beam irradiating the second part of the second half of the detector, and the cycle time of operation is equal to two times the read out time, or is 4 times exposure time (readout time during exposure) whichever is longer, opposed to one exposure time plus one readout time, multiplied by four. The cycle rate is thus slower for the case where 2 X-ray beams simultaneously irradiate one half of the detector and then the other half of the detector, but the advantage is that there is less scatter and thus a better signal to noise ratio, and even no cross scatter in certain situations, for example when pulses of X-ray radiation are sequentially received. Further irradiation possibilities can be achieved, with 6 X-ray beams irradiating a detector with reduced cross scatter, with the cycle time of operation being three time the read out time (or six times the exposure time as discussed above, whichever is longer), and 8 X-ray beams irradiating a detector with reduced cross scatter, where of those 8 X-ray beams a first pair of beams irradiate the detector simultaneously and a second pair of beams irradiate the detector simultaneously, with the remaining 4 X-ray beams irradiating the detector at different times, and the cycle time of operation is equal to three times the read out time or the cycle time in this case is 6 exposure times plus one readout time, whichever is longer.

In other words, the detector can be partitioned into halves and those halves further partitioned into halves, providing extra flexibility where exposures can be separated in time to reduce and/or avoid the effects of cross scatter, while the halves of the detector can still be read out together, and where one half of the detector can be read out whilst the other half is being irradiated.

In this manner, an apparatus is provided that utilizes a detector operating with frame transfer applied to different parts of the detector, with read out of data of one part of the detector being enabled alongside simultaneous irradiation of another part of the detector.

Frame transfer can be described as follows: The collected signal in the pixel must be readout or stored before any other operation (like reset or new signal collection) destroys the signal. When the readout phase takes a relatively long time it can be beneficial to store the pixel signal on a storage node in the pixel. Storing the pixel signal on a storage node is normally done with a so called sample & hold circuit. When the copy process is completed the original signal can be destroyed. One can also transfer the pixel signal (charge) to a storage capacitor. The frame transfer, as applied here for the different detector partitioned schemes, is used to make a copy of, or transfer, the pixel signal to one or more storage nodes in the pixel to enable the signal to be readout at a later time.

According to the first example, the X-ray detector comprises at least one reset, the at least one reset configured to reset the plurality of first pixels and configured to reset the plurality of second pixels. The X-ray detector is configured such that the first radiation emitted by the at least one X-ray source is receivable by the portion of first pixels before the at least one reset resets the plurality of second pixels. The detector is also configured such that the at least one reset resets the plurality of second pixels before the second radiation emitted by the at least one X-ray source is receivable by the portion of second pixels.

In other words, a first area of a detector (that has first pixels) can be irradiated. Then a reset can applied to a second area of the detector (that has second pixels). In this manner, any cross scatter signal in the second area can be erased. Then, the second area can be irradiated, enabling an accurate signal to be acquired. Also, because signals generated in the first pixels (of the first area) can be stored in at least one plurality of storage nodes (e.g., a sample and hold circuit) a reset can be applied to one part of the detector while having a sample and hold phase applied to another part of the detector. Thus, this enables signals to be read-out from one part of the detector whilst another part of the detector is irradiated. In an example, the X-ray detector comprises at least one first read out associated with the at least one first plurality of storage nodes and at least one second read out associated with the at least one second plurality of storage nodes. The at least one first read out is configured to read out the plurality of first signals and the at least one second read out is configured to read out the plurality of second signals. The detector is configured such that the second radiation emitted by the at least one X-ray source is receivable by the portion of second pixels before read out of the plurality of the first signals has finished.

In an example, the X-ray detector is configured such that the second radiation emitted by the at least one X-ray source is receivable by the portion of second pixels before the at least one reset resets the plurality of first pixels, and the X-ray detector is configured such that the at least one reset resets the plurality of first pixels before a third radiation emitted by the at least one X-ray source is receivable by the portion of first pixels.

In other words, a first area of a detector (that has first pixels) can be irradiated by a first source (or an extended with apertures and/or shutters or a moving source). Then a reset can be applied to a second area of the detector (that has second pixels). In this manner, any cross scatter signal in the second area due to irradiation of the first area can be erased. Then, the second area can be irradiated with the second source (or an extended with apertures and/or shutters or a moving source), enabling an accurate signal to be acquired. Also, because signals generated in the first pixels (of the first area) can be stored in at least one plurality of storage nodes (e.g., a sample and hold circuit) a reset can be applied to one part of the detector while having a sample and hold phase applied to another part of the detector. Thus, this enables signals to be read-out from the first area of the detector whilst the second area of the detector is irradiated. Irradiation of the second part of the detector will lead to a cross scatter signal in the first area (which has first pixels). Therefore, by applying a reset to the first area, any cross scatter signal in the first area due to irradiation of the second area can be erased. Then, the first area can be irradiated (again) with the first source, enabling an accurate signal to be acquired. Also, because signals generated in the second pixels (of the second area) can be stored in at least one plurality of storage nodes (e.g., a sample and hold circuit) a reset can be applied to the first area of the detector while having a sample and hold phase applied to the second area of the detector. In this manner, the detector of the apparatus can be operated in a cyclical manner, acquiring imagery in a movie like manner.

Here, a third pulse of radiation means a pulse of radiation that can be emitted by the at least one X-ray source, that is different to the first radiation and different to the second radiation.

In an example, the first and third radiations are emitted by different X-ray sources. In an example, the first and third radiations are emitted by the same X-ray source. In an example, the first and second radiations are emitted by the same X-ray source that is at one spatial position for emission of the first radiation and is at a second spatial position for emission of the second radiation, and the X-ray source returns to the original position to emit the third radiation (in other words, the X-ray source can be moveable in this example). In an example, the X-ray detector is configured such that the third radiation emitted by the at least one X-ray source is receivable by the portion of first pixels before read out of the plurality of the second signals has finished.

In another aspect, there is provided an X-ray detector for imaging an object. The X-ray detector comprises a plurality of X-ray radiation detecting areas. The plurality of X-ray detecting areas comprising a first area, comprising a plurality of first pixels, and a second area, comprising a plurality of second pixels. First radiation emitted by at least one X-ray source is receivable by at least a portion of the first pixels, and second radiation emitted by the at least one X-ray source is receivable by at least a portion of the second pixels. The X-ray detector is configured such that the X-ray radiation received by a pixel leads to the generation of signal in that pixel. The X-ray detector comprises at least one first plurality of storage nodes associated with the first area and at least one second plurality of storage nodes associated with the second area. The at least one first plurality of storage nodes is configured to store a plurality of first signals representative of corresponding signals on the plurality of first pixels and the at least one second plurality of storage nodes is configured to store a plurality of second signals representative of corresponding signals on the plurality of second pixels. The at least one second plurality of storage nodes is configured to store the plurality of second signals after the at least one first plurality of storage nodes is configured to store the plurality of first signals. The X-ray detector comprises at least one reset, the at least one reset configured to reset the plurality of first pixels and configured to reset the plurality of second pixels. The X-ray detector is configured such that the first radiation emitted by the at least one X-ray source is receivable by the portion of first pixels before the at least one reset resets the plurality of second pixels. The detector is also configured such that the at least one reset resets the plurality of second pixels before the second radiation emitted by the at least one X-ray source is receivable by the portion of second pixels.

In other words, the X-ray detector can be used in 4D imaging an object. According to another aspect, there is provided a method for imaging of an object, comprising:

a) receiving by at least a portion of first pixels of a first area of an X-ray detector first radiation emitted by at least one X-ray source, wherein the X-ray detector is configured such that X-ray radiation received by a pixel leads to the generation of signal in that pixel;

b) storing, in at least one first plurality of storage nodes associated with the first area, a plurality of first signals representative of corresponding signals on the plurality of first pixels;

e) after step a), receiving by at least a portion of second pixels of a second area of the X-ray detector second radiation emitted by the at least one X-ray source; and g) storing, in at least one second plurality of storage nodes associated with the second area, a plurality of second signals representative of corresponding signals on the plurality of second pixels.

In other words, the method can be used for 4D imaging an object. In other words, a detector is provided with partitioned frame transfer for different parts of the detector with frame transfer for one part being independent from frame transfer for a second part.

In this manner, the time between different X-ray beams passing through the object can be minimised leading to a reduction in the detrimental effects of object movement during examination, and the effects of cross scattering can be minimised.

To put this another way, in an example a first X-ray beam can pass through the object and irradiate a first part of a first area of the detector. Part of a first storage node circuit (sample and hold circuit) can then store the signals on the pixels of the first part of the first area of the detector. Then a second X-ray beam can pass through the object and irradiate a second part of the first area of the detector. Another part of the first storage node circuit (sample and hold circuit) can then store the signals on the pixels of the second part of the first area of the detector. As discussed above, this second part of the first area will be contaminated with cross scatter from the first X-ray beam. This cross scatter can be removed if both exposures irradiate different areas. The signals associated with the first area of the detector can then be read out. However, at the same time as read out, a second area of the detector can be irradiated, where a third X-ray beam can pass through the object and irradiate a first part of the second area of the detector. Part of a second storage node circuit (sample and hold circuit) can then store the signals on the pixels of the first part of the second area of the detector. Then a fourth X-ray beam can pass through the object and irradiate a second part of the second area of the detector. Another part of the second storage node circuit (sample and hold circuit) can then store the signals on the pixels of the second part of the second area of the detector. The signals associated with the second area of the detector can then be read out, and at the same time irradiation of the first area of the detector can commence again. In an example, the first and second X-ray beams can be applied contemporaneously, where a single storage node circuit (sample and hold circuit) can be used to store the associated signals. In an example, the third and fourth X-ray beams can be applied contemporaneously, where a single storage node circuit (sample and hold circuit) can be used to store the associated signals.

In this manner, part of a detector can be read out while at the same time another part of the detector is irradiated.

In this way, fast imaging with good image quality (motions artefacts and cross-scatter minimized) is provided. This can be utilized in a wide angle 2-dimensional source configuration with a single detector, and can be used for 4D imaging.

To put this another way, because not all X-ray beams use the same detector area, information associated with a first beam can be stored in one (or several) sub-frame transfer(s) followed immediately by a second beam etc. Once the detector area, not necessarily the whole detector, has been exposed (and all information is safely stored) the detector area can be read out. Only certain sub-areas can be exposed, and either the whole detector read out all or only that part of the detector containing information.

According to this aspect of the method, the method comprises:

c) after step a) and before step e), resetting the plurality of second pixels.

In other words, reset can be applied to one part of the detector while having a sample and hold phase applied to another part of the detector. Both reset and sample and hold take a certain amount of time, and in this manner operation of the apparatus is speeded up.

In this manner, numerous views of an object, such as a beating heart, can be provided with motion artefacts minimized and with cross scattering reduced or avoided, through having a detector area partitioned in various sub-areas, whereby each sub-area can have its own sub-frame transfer, can have its own reset and can have its own sub-frame read-out.

In an example, resetting the plurality of second pixels also resets the plurality of first pixels.

In other words, a global reset can be applied across the detector, thereby leading to a simplified device that does not need to have a partitioned reset.

In an example, the method comprises:

d) after step b), reading out by at least one first read out associated with the at least one first plurality of storage nodes the plurality of first signals; and wherein step e) commences before step d) has finished.

In other words, by using partitioned frame transfer signals from a first part of the detector can be acquired and transferred or copied (stored) in a sample and hold, and then immediately a second part of the detector can be irradiated whilst the sample and hold associated with the first part is read out. In this manner, the time taken to acquire and read out a detector useable for imaging, such as for 4D imaging, is reduced.

To put this another way, in an example a detector with frame transfer is partitioned into an upper panel half A and the lower panel half B (dual block frame transfer). A part of A can be exposed, and once the exposure of A has finished and data stored safely in a sample and hold, immediately read-out of A from the sample and hold can start and at the same time a reset of B is used to eliminate the cross scatter caused during irradiation of A and following which B can be exposed. Once read-out of A is finished and the exposure B is finished and safely stored in a sample and hold, a reset of A can be used following which A can be exposed again. In an example, the detector panel can be partitioned into more subareas giving correspondingly more possibilities for the switching schemes that can be applied. In an example, the method comprises:

f) after step e), resetting the plurality of first pixels; and i) after step f), receiving by the portion of first pixels of the first area of the X-ray detector a third radiation emitted by the at least one X-ray source.

In other words, resetting can be applied to one part of the detector while having a sample and hold phase applied to another part of the detector. Both resetting and sample and hold take a certain amount of time, and in this manner operation of the apparatus is speeded up.

In an example, the method comprises:

h) after step g), reading out by at least one second read out associated with the at least one second plurality of storage nodes the plurality of second signals; and wherein step i) commences before step h) has finished.

In an example, the method comprises the following:

step a) comprises:

a1) receiving by a first sub-portion of first pixels of the first area of the X-ray detector radiation emitted by an X-ray source; and a2) receiving by a second sub-portion of first pixels of the first area of the X-ray detector radiation emitted by an X-ray source different to the X-ray source in step a1; and wherein the at least one first plurality of storage nodes comprises at least two plurality of storage nodes, and step b) comprises:

b1) storing, in a plurality of storage nodes associated with the first area, a plurality of first signals representative of corresponding signals on the first sub-portion of first pixels; and b2) storing, in a plurality of storage nodes associated with the first area, a plurality of first signals representative of corresponding signals on the second sub-portion of first pixels, wherein the plurality of storage nodes in step b2 is different to the plurality of storage nodes in step b1; and step c) comprises:

c1) after step a1), resetting the plurality of first pixels, and after step a2) resetting the plurality of second pixels; and step e) comprises:

e1) receiving by a first sub-portion of second pixels of the second area of the X-ray detector radiation emitted by an X-ray source; and e2) receiving by a second sub-portion of second pixels of the second area of the X-ray detector radiation emitted by an X-ray source different to the X-ray source in step e1; and wherein the at least one second plurality of storage nodes comprises at least two plurality of storage nodes, and step g) comprises:

g1) storing, in a plurality of storage nodes associated with the second area, a plurality of second signals representative of corresponding signals on the first sub-portion of second pixels; and g2) storing, in a plurality of storage nodes associated with the second area, a plurality of second signals representative of corresponding signals on the second sub-portion of second pixels, wherein the plurality of storage nodes in step g2 is different to the plurality of storage nodes in step g1.

According to another aspect, there is provided a computer program element controlling apparatus as previously described which, in the computer program element is executed by processing unit, is adapted to perform the method steps as previously described. According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
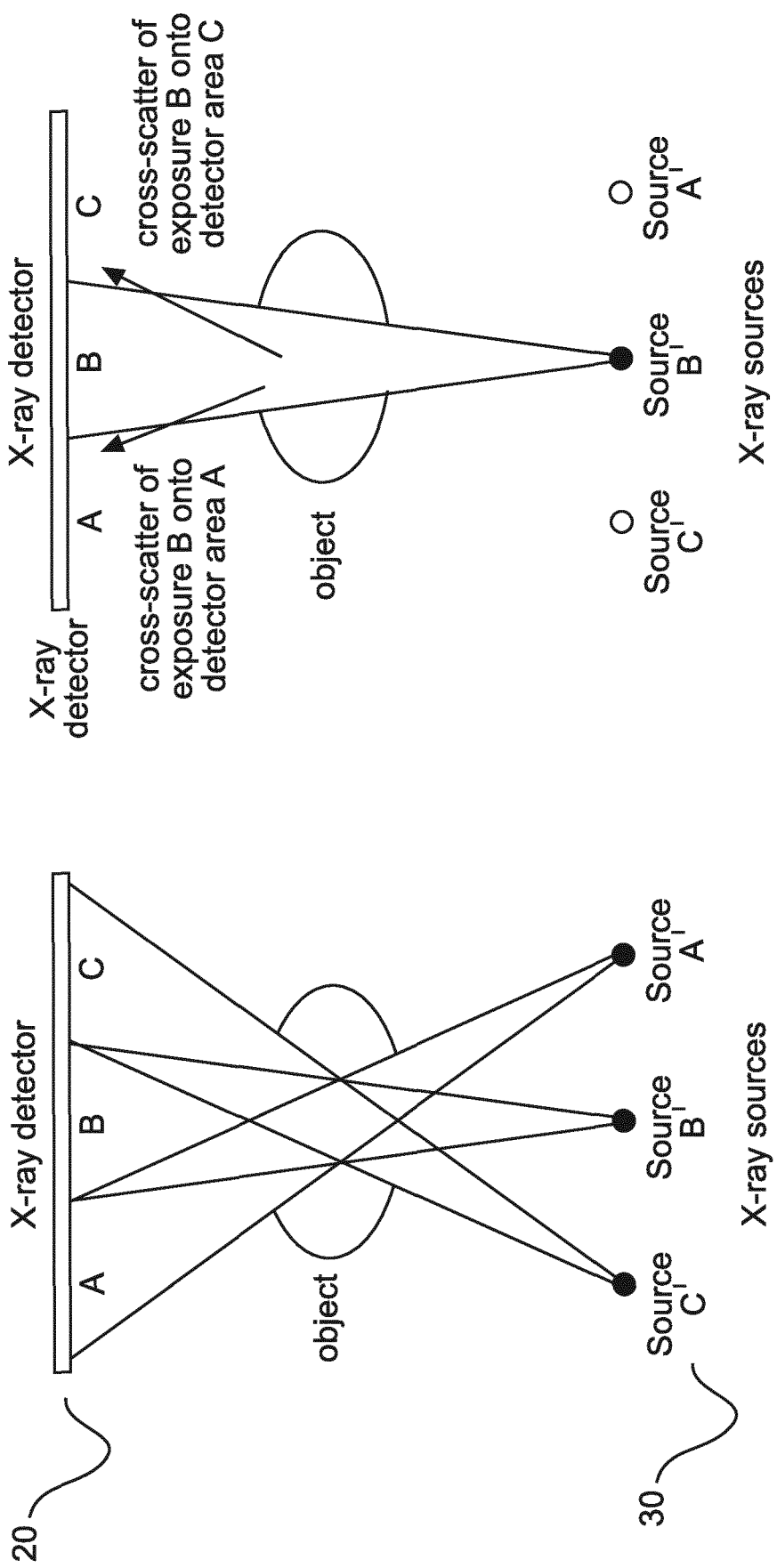
FIG. 1 shows a schematic set up of an example of an apparatus for imaging an object.

FIG. 1 shows an example of an apparatus for imaging an object and indicates what is meant by "cross-scatter". The apparatus has three X-ray sources A', B' and C' and corresponding X-ray beams are produced which pass roughly through the same region of an object being imaged. Rather than three X-ray sources, an extended X-ray source could be provided which is appropriately shuttered and/or apertured. The object is placed between the X-ray sources and an X-ray detector. The X-ray beams generated from sources A', B' and C' fall on separate regions A, B, and C of the detector respectively. Separate images in regions A, B, and C of the detector can be appropriately combined to form a 3D image of the object in a known manner. The then "3D" relates to the three coordinates x, y, and z in a Cartesian coordinate system or to the three coordinates r, θ and ρ in a Spherical coordinate system for example. The time period over which the beams illuminated the object then provides a "moment" or snap shot in time, and provides for the fourth dimension of "time" in 4D imaging. However, X-rays that are generated from source B' and are arranged to fall on detector area B, will suffer a certain amount of scattering in the object and some X-rays will scatter onto area A of the detector and some onto area C of the detector. This is called cross-scatter and serves to degrade the images obtained in the respective regions of the detector. This will then lead to a degradation in the imaging. The apparatus can be used for 4D imaging an object.

Figure 2:
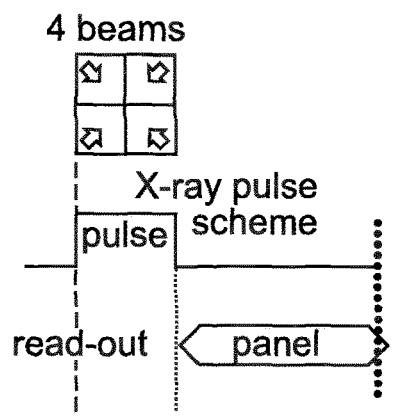
FIG. 2 shows schematic diagrams, and associated timing diagram, of a detector that can be used in imaging an object.
Figure 2:
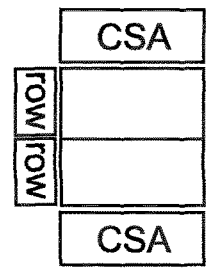
Figure 2:
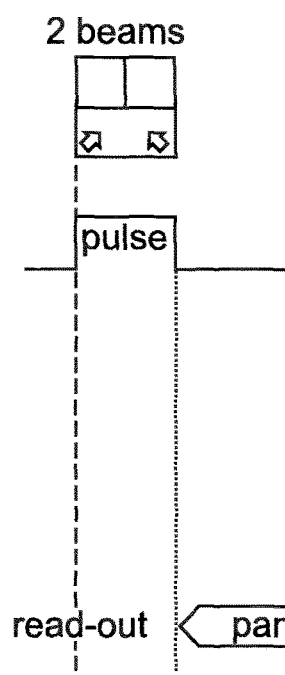
Figure 2:
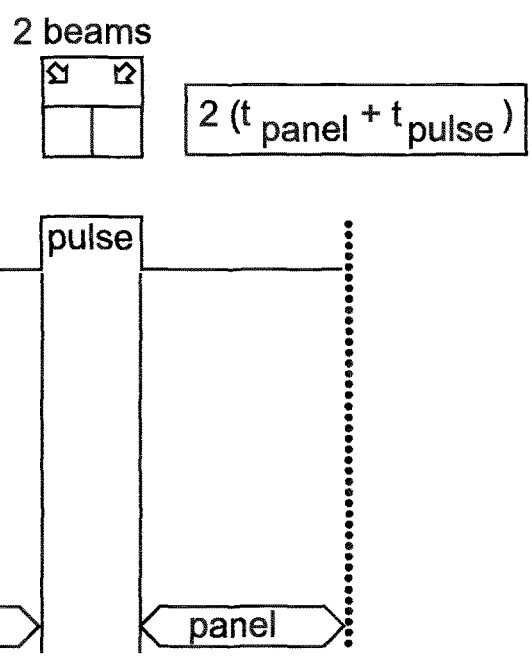
Figure 2:
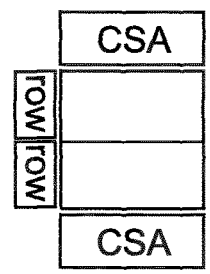

FIG. 2 shows in the upper portion of the figure an example of a detector that can be used in imaging an object, and can be used in 4D imaging an object. Four X-ray beams are produced in a similar manner to that discussed with reference to FIG. 1, and these fall on four separate regions of an X-ray detector, as shown in the upper left part of FIG. 1. The four X-ray beams illuminate the detector at the same time, or over the same time period when the detector is configured to generate a signal from incident X-rays. This is termed as a "pulse" period having a duration $t_{pulse}$. The signals on the detector are then read out, with this termed as a "panel" period that occurs after the pulse period, and has a duration $t_{panel}$. The cycle time of such a detector, in providing imaging, is then equal to a time having a duration $t_{panel}+t_{pulse}$. The advantage of such a detector is that all the beams pass through the object at the same instance in time, and therefore there will be no relative motion artifacts caused by the object moving between respective beam illuminations. However, as discussed above with reference to FIG. 1, the images will suffer from cross-scatter.

FIG. 2 shows in the lower portion of the figure another example of a detector that can be used in imaging an object, such as for 4D imaging. Two of the four X-ray beams discussed above now irradiate one half of the detector. The detector is then read out. The other two beams of the four X-ray beams now irradiate the other half of the detector, and the detector is read out. The cycle time of such a detector, in providing imaging, is then equal to a time having a duration $2t_{panel}+2t_{pulse}$. The advantage of such a detector is that there is reduced cross scatter, with the disadvantage being that the time needed for the sequence is doubled over that for apparatus of FIG. 2.

Figure 3:
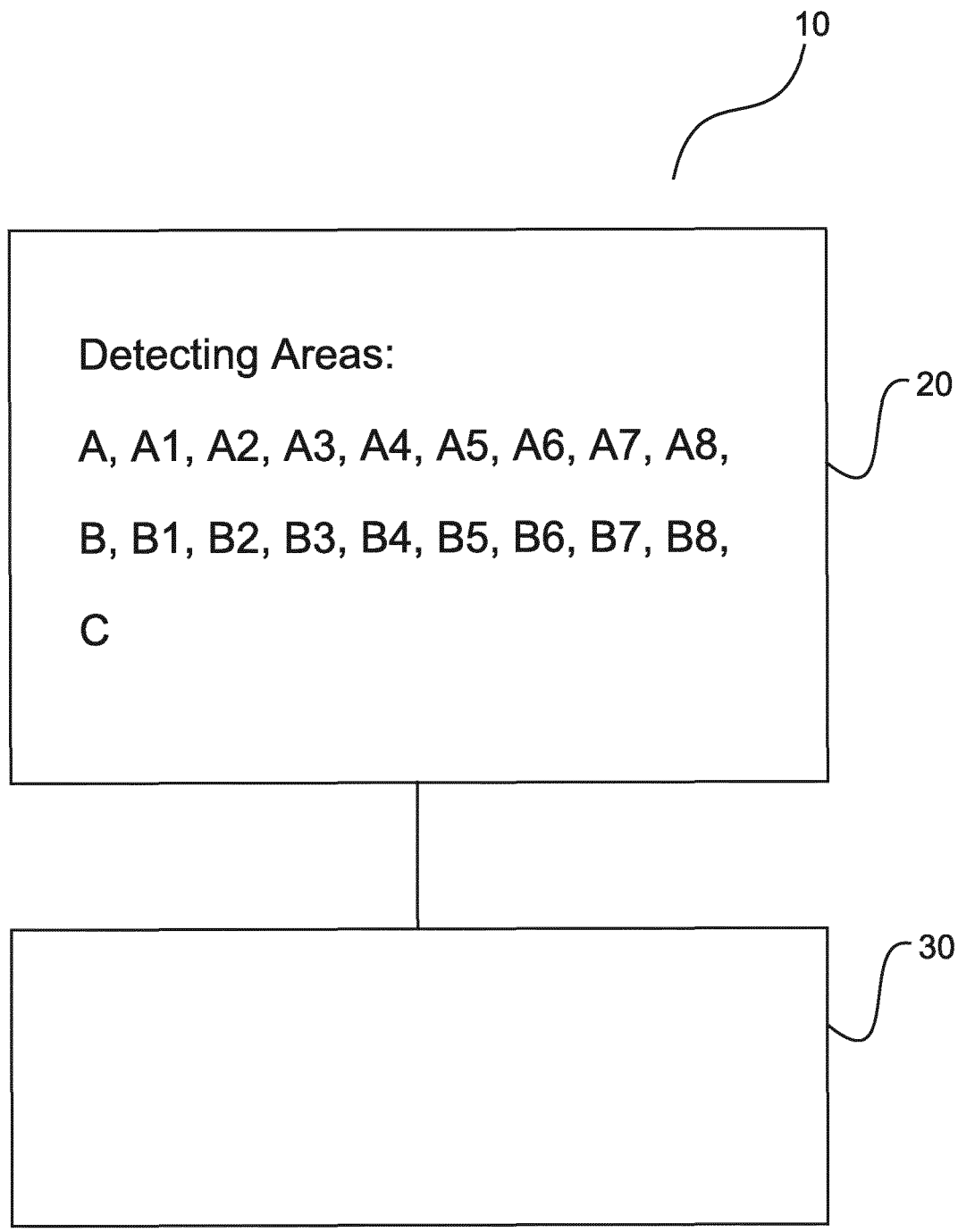
FIG. 3 shows a schematic diagram of an apparatus for imaging an object.

FIG. 3 shows an example of an apparatus 10 for imaging an object, such as for 4D imaging. The apparatus 10 comprises an X-ray detector 20, and at least one X-ray source 30. The at least one X-ray source 30 is configured to be positioned relative to the X-ray detector 20 such that at least a part of the region between the at least one X-ray source 30 and the X-ray detector 20 is an examination region for accommodating an object. The X-ray detector 20 comprises a plurality of X-ray radiation detecting areas A, A1, A2, A3, A4, A5, A6, A7, A8; B, B1, B2, B3, B4, B5, B6, B7, B8; C. The plurality of X-ray detecting areas comprising a first area A, A1, A2, A3, A4, A5, A6, A7, A8 comprising a plurality of first pixels and a second area B, B1, B2, B3, B4, B5, B6, B7, B8; C comprising a plurality of second pixels. A first radiation emitted by the at least one X-ray source 30 is receivable by at least a portion of the first pixels, and a second radiation emitted by the at least one X-ray source 30 is receivable by at least a portion of the second pixels. The X-ray detector 20 is configured such that the X-ray radiation received by a pixel leads to the generation of signal in that pixel. The X-ray detector 20 comprises at least one first plurality of storage nodes associated with the first area and at least one second plurality of storage nodes associated with the second area. The at least one first plurality of storage nodes is configured to store a plurality of first signals representative of corresponding signals on the plurality of first pixels. The at least one second plurality of storage nodes is configured to store a plurality of second signals representative of corresponding signals on the plurality of second pixels. The at least one second plurality of storage nodes is configured to store the plurality of second signals after the at least one first plurality of storage nodes is configured to store the plurality of first signals.

In an example, the at least one X-ray source is a plurality of X-ray sources. In an example, the plurality of X-ray sources comprises a first X-ray source and a second X-ray source. In an example, radiation emitted by the first X-ray source is receivable by at least a portion of the first pixels, and radiation emitted by the second X-ray source is receivable by at least a portion of the second pixels.

In other words, in an example the first radiation is emitted by one X-ray source and the second radiation is emitted by another X-ray source, or in another example these are emitted by the same X-ray source.

In an example, the X-ray source is an extended X-ray source, configured to emit radiation from different spatial positions, through for example the use of apertures. In an example, the X-ray source is moveable, such that it is configured to emit radiation from different spatial positions.

In an example, the signal generated in a pixel is a charge.

In an example, the at least one plurality of storage nodes is at least one plurality of sample and holds. In other words, a sample and hold is just a form of storage node. In an example, each pixel has its own sample and hold (storage node). In an example, control of this at least one plurality of storage nodes groups the at least one plurality of storage nodes to one of the detector areas.

In an example, "dual block" frame transfer works most efficiently when separate halves of the detector are exposed alternatively. In an example, "quad block" frame transfer gives extra flexibility, enabling efficient exposure schemes, with split rows giving even more flexibility.

According to an example, the X-ray detector 20 comprises at least one reset. The at least one reset configured to reset the plurality of first pixels and configured to reset the plurality of second pixels. wherein the detector is configured such that the first radiation emitted by the at least one X-ray source is receivable by the portion of first pixels before the at least one reset resets the plurality of second pixels and the detector is configured such that the at least one reset resets the plurality of second pixels before the second radiation emitted by the at least one X-ray source is receivable by the portion of second pixels.

In an example, the at least one reset is configured to reset the plurality of first pixels.

In an example, the at least one reset is configured to reset the plurality of first pixels at the same time as it resets the plurality of second pixels.

In an example, a detector with partitioned frame transfer has part A with its own frame transfer and part B with its own frame transfer. If detector part B is exposed (meaning: the X-ray beam goes through the object, e.g. patient, and lands on detector part B giving a 2D image of the object—image B), then normally some X-rays are scattered in or at the object and land onto detector area A. This kind of scatter is called cross scatter, where now if a different beam goes through the object and lands on detector part A the signal will be augmented by that scattered during exposure detector part B, and degrade image A. However, after exposure of detector part B and before exposure of detector part A, detector part A can be reset either by a reset that applies only to detector part A or by a global reset and this eliminates the cross scatter signal.

According to an example, the X-ray detector 20 comprises at least one first read out associated with the at least one first plurality of storage nodes and at least one second read out associated with the at least one second plurality of storage nodes. The at least one first read out is configured to read out the plurality of first signals and the at least one second read out is configured to read out the plurality of second signals. The X-ray detector is configured such that the second radiation emitted by the at least one X-ray source is receivable by the portion of second pixels before read out of the plurality of the first signals has finished.

According to an example, the X-ray detector 20 is configured such that the second radiation emitted by the at least one X-ray source is receivable by the portion of second pixels before the at least one reset resets the plurality of first pixels. The X-ray detector is also configured such that the at least one reset resets the plurality of first pixels before a third radiation emitted by the at least one X-ray source is receivable by the portion of first pixels. According to an example, the X-ray detector 20 is configured such that the third radiation emitted by the at least one X-ray source is receivable by the portion of first pixels before read out of the plurality of the second signals has finished.

In an example, the apparatus comprises an output unit configured to output data representative of the object.

In an example, the system is a C-arm arrangement, or a CT arrangement or a tomosynthesis arrangement.

According to an example, an X-ray detector 20 for imaging an object, comprises a plurality of X-ray radiation detecting areas A, A1, A2, A3, A4, A5, A6, A7, A8; B, B1, B2, B3, B4, B5, B6, B7, B8; C. The plurality of X-ray detecting areas comprising a first area A, A1, A2, A3, A4, A5, A6, A7, A8 comprising a plurality of first pixels and a second area B, B1, B2, B3, B4, B5, B6, B7, B8; C comprising a plurality of second pixels. First radiation emitted by at least one X-ray source is receivable by at least a portion of the first pixels, and second radiation emitted by the at least one X-ray source is receivable by at least a portion of the second pixels. The X-ray detector is configured such that the X-ray radiation received by a pixel leads to the generation of signal in that pixel. The X-ray detector comprises at least one first plurality of storage nodes associated with the first area and at least one second plurality of storage nodes associated with the second area. The at least one first plurality of storage nodes is configured to store a plurality of first signals representative of corresponding signals on the plurality of first pixels and the at least one second plurality of storage nodes is configured to store a plurality of second signals representative of corresponding signals on the plurality of second pixels. The at least one second plurality of storage nodes is configured to store the plurality of second signals after the at least one first plurality of storage nodes is configured to store the plurality of first signals. The detector can be used for 4D imaging an object.

Figure 4:
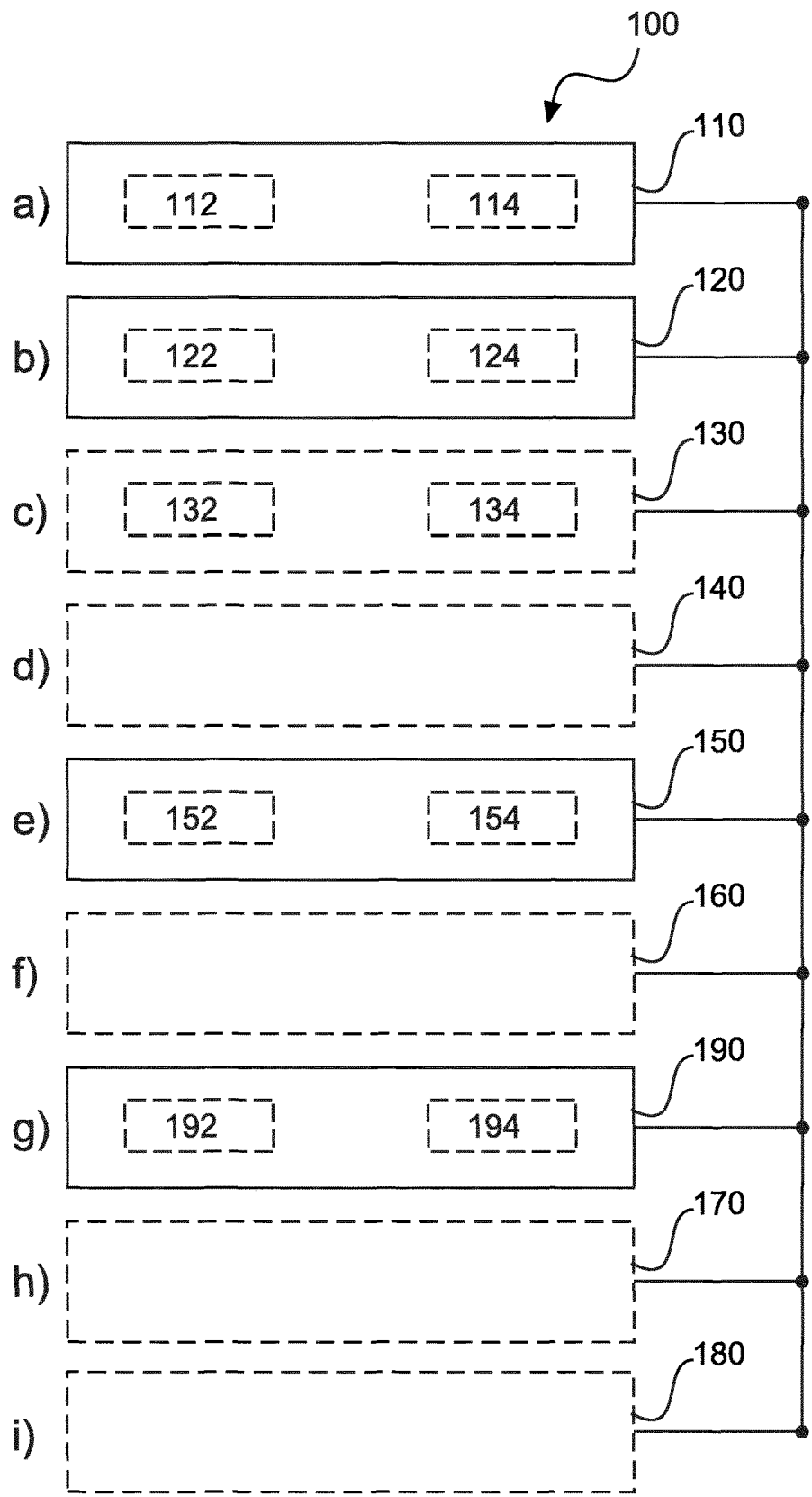
FIG. 4 shows a method for imaging an object.

FIG. 4 shows an example of a method 100 for imaging of an object in its basic steps. The methods comprises:

In a receiving step 110, also referred to as step a), first radiation emitted by at least one X-ray source 30 is received by at least a portion of first pixels of a first area A, A1, A2, A3, A4, A5, A6, A7, A8 of an X-ray detector 20, wherein the X-ray detector is configured such that X-ray radiation received by a pixel leads to the generation of signal in that pixel.

In a storing step 120, also referred to as step b), a plurality of first signals representative of corresponding signals on the plurality of first pixels are stored in at least one first plurality of storage nodes associated with the first area.

After step a), in a receiving step 150, also referred to as step e), second radiation emitted by the at least one X-ray source 30 is received by at least a portion of second pixels of a second area B, B1, B2, B3, B4, B5, B6, B7, B8; C of the X-ray detector. In a storing step 190, also referred to as step g), a plurality of second signals representative of corresponding signals on the plurality of second pixels are stored in at least one second plurality of storage nodes associated with the second area.

The method 100 can be used for 4D imaging an object.

In an example, step e) is after step b).

In an example, the X-ray detector is provided with 4 areas, each having independent frame transfer. In an example, the detector is provided with 4 areas in a 2×2 geometry. In an example, the detector is provided with 4 areas in a 4×1 geometry. In an example, the detector is provided with n×m areas in an n×m geometry.

According to an example, the method comprises:

After step a) and before step e), in a resetting step 130, also referred to as step c), the plurality of second pixels is reset.

In an example while step b) is being executed and during execution of step b) execution of step c) is commenced.

In an example while step c) is being executed and during execution of step c) execution of step b) is commenced.

In an example, the reset only applies to the plurality of second pixels. In other words, the reset is partitioned across the detector.

According to an example, resetting the plurality of second pixels also resets the plurality of first pixels.

In other words, a global reset can be applied across the detector, thereby leading to a simplified device that does not need to have a partitioned reset.

According to an example, the method comprises: After step b), in a reading out step 140, also referred to as step d), reading out by at least one first read out associated with the at least one first plurality of storage nodes the plurality of first signals; and wherein step e) commences before step d) has finished. In an example, a single read out is configured to read out signals associated with more than one sample and hold associated with the first area of the detector. In an example, a single read out is configured to read out signals associated with more than one sample and hold associated with the second area of the detector.

According to an example, the method comprises:

After step e), in a resetting step 160, also referred to as step f) the plurality of first pixels are reset; and After step f, in a receiving step 180, also referred to as step i), third radiation emitted by the at least one X-ray source is received by the portion of first pixels of the first area of the X-ray detector.

In an example, step i) is after step g).

In an example while step f) is being executed and during execution of step f) execution of step g) is commenced.

In an example while step g) is being executed and during execution of step g) execution of step f) is commenced.

In an example, resetting only applies to the plurality of first pixels. In other words, the reset is partitioned across the detector.

According to an example, the method comprises:

After step g), in a reading out step 170, also referred to as step h), reading out by at least one second read out associated with the at least one second plurality of storage nodes the plurality of second signals; and wherein step i) commences before step h) has finished.

According to an example, step a) comprises:

a1) receiving 112 by a first sub-portion of first pixels of the first area of the X-ray detector radiation emitted by an X-ray source A1; and a2) receiving 114 by a second sub-portion of first pixels of the first area of the X-ray detector radiation emitted by an X-ray source A2 different to the X-ray source in step a1; and wherein the at least one first plurality of storage nodes comprises at least two plurality of storage nodes, and wherein step b) comprises:

b1) storing 122, in a plurality of storage nodes SHA1 associated with the first area, a plurality of first signals representative of corresponding signals on the first sub-portion of first pixels; and b2) storing 124, in a plurality of storage nodes SHA2 associated with the first area, a plurality of first signals representative of corresponding signals on the second sub-portion of first pixels, wherein the plurality of storage nodes in step b2 is different to the plurality of storage nodes in step b1; and wherein step c) comprises:

c1) after step a1), resetting 132 the plurality of first pixels, and after step a2) resetting 134 the plurality of second pixels; and wherein step e) comprises:

e1) receiving 152 by a first sub-portion of second pixels of the second area of the X-ray detector radiation emitted by an X-ray source B1; and e2) receiving 154 by a second sub-portion of second pixels of the second area of the X-ray detector radiation emitted by an X-ray source B2 different to the X-ray source in step e1; and wherein the at least one second plurality of storage nodes comprises at least two plurality of storage nodes, and wherein step g) comprises:

g1) storing 192, in a plurality of storage nodes SHB1 associated with the second area, a plurality of second signals representative of corresponding signals on the first sub-portion of second pixels; and g2) storing 194, in a plurality of storage nodes SHB2 associated with the second area, a plurality of second signals representative of corresponding signals on the second sub-portion of second pixels, wherein the plurality of storage nodes in step g2 is different to the plurality of storage nodes in step g1.

In an example, the at least one first read out comprises read out ROA1 configured to read out the plurality of storage nodes (sample and hold circuit) SHA1 and the at least one first read out comprises read out ROA2 configured to read out the plurality of storage nodes (sample and hold circuit) SHA2.

In an example, a reset is applied between steps a1 and a2.

In an example, a reset is applied between steps e1 and e2.

In an example, the at least one second read out comprises read out ROB1 configured to read out the plurality of storage nodes (sample and hold circuit) SHB1 and the at least one second read out read out ROB2 configured to read out plurality of storage nodes (sample and hold circuit) SHB2.

In an example, the reset can apply to the first sub-portion of first pixels and not to other pixels of the detector. In an example, the reset can apply to the second sub-portion of first pixels and not to other pixels of the detector. In an example, the reset can apply to the first sub-portion of second pixels and not to other pixels of the detector. In an example, the reset can apply to the second sub-portion of second pixels and not to other pixels of the detector. In an example, all other combinations are possible, in that 1, 2, 3, or all 4 areas of the detector can have a reset applied. In other words, the reset in one areas of the detector can be applied independently of the reset in other areas of the detector.

Examples of the apparatus and method for imaging an object will now be described in more detail in conjunction with FIGS. 5-12, where a detector is used with partitioned frame transfer for imaging to minimize both motion artifacts of an object and cross-scatter. The examples of the apparatus and method can be used for 4D imaging.

Figure 5:
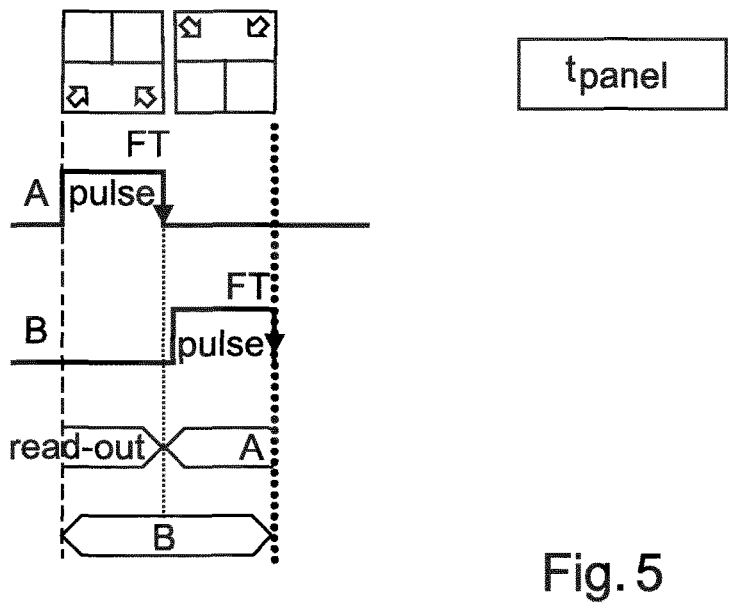
FIG. 5 shows a schematic diagram, and associated timing diagram, of a detector for imaging an object.
Figure 5:
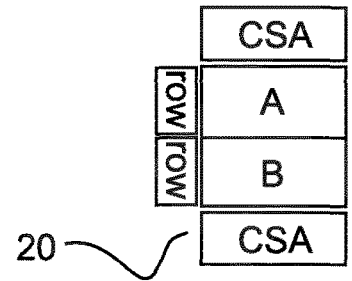

FIG. 5 shows an example of a detector with dual block frame transfer, where an amplifier is used that in one example can read out a voltage and in another example read out charge. In other words an output Amplifier (Amp) is used, which in one example is a charge sensitive amplifier (CSA) as shown in FIG. 5. Two x-ray beams illuminate the area A of the detector and frame transfer is applied after illumination and two x-ray beams illuminate the area B of the detector and frame transfer is applied after illumination. Partitioning the frame transfer (and reset) for lower and upper panels (area A and area B respectively) gives two panel halves with independent frame transfer and read out. After an area is illuminated, frame transfer is applied that copies or transfers the charge on detector pixels to a sample and hold, and a reset is applied. As discussed above, during illumination cross scatter will lead to other areas of the detector suffering irradiation. The reset, resets or wipes clean the charge, or otherwise makes the other area or areas of the detector ready for the acquisition of a signal associated with another radiation beam, but now with no cross scatter signal. The reset can be applied globally, i.e. to all detector areas or to the area or areas that are to now be irradiated. This enables area A to be read out after it has been illuminated, and enables area B to be read out after it has been illuminated. In this manner, area A can be read out and during that read out area B can be illuminated and vice versa. Within individual panel readout, with the associated duration being $t_{panel}$, the cycle time of such a detector, in providing imaging, such as 4D imaging, is then equal to a time having a duration $t_{panel}$. This means the same advantages as if two separate detectors with frame transfer are provided, with further advantages being provided such as there being no gap between the two detector areas (enabling central exposures), and providing for a compact and cost-effective solution.

Figure 6:
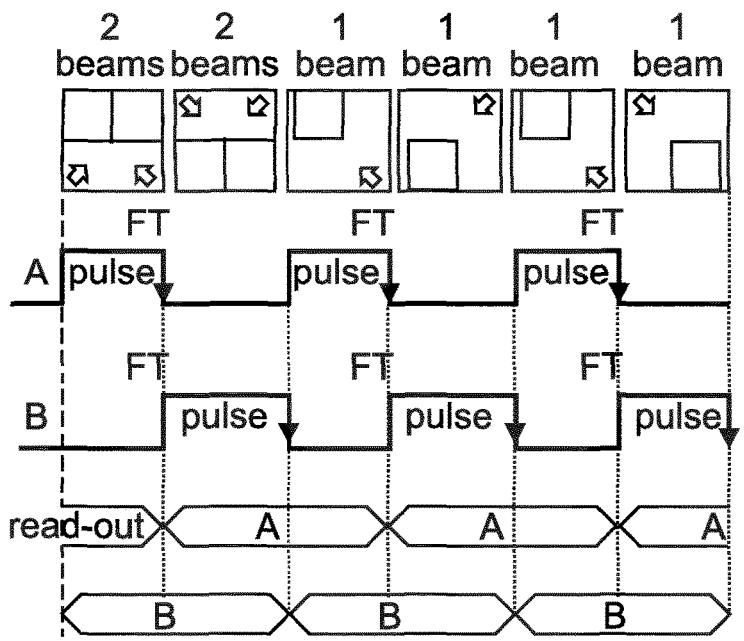
FIG. 6 shows a schematic diagram, and associated timing diagram, of a detector for imaging an object.
Figure 6:
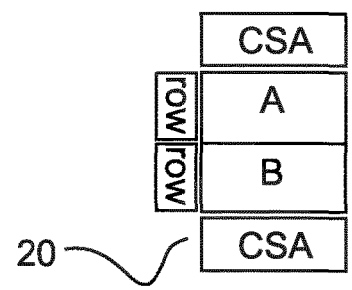

FIG. 6 shows an example of a detector with dual block frame transfer, but with eight beams passing through the object. In the following, after each illumination of a detector area frame transfer is applied. Thus, two beams illuminate area A of the detector, with frame transfer applied and that area then being read out. During read out of area A, two beams irradiate area B, with frame transfer being applied and that area then being read out. A part of area A is illuminated with a single x-ray beam following which frame transfer is applied and area A is read out, and during read out of area A, area B is illuminated following which frame transfer is applied and it is read out. Finally, a part of area A is illuminated with a single x-ray beam, following which area B is illuminated with a single x-ray beam with these areas having frame transfer applied and being read out as described above. In this manner, the cycle time of such a detector is three times the read out time of a panel ($3t_{panel}$).

Figure 7:
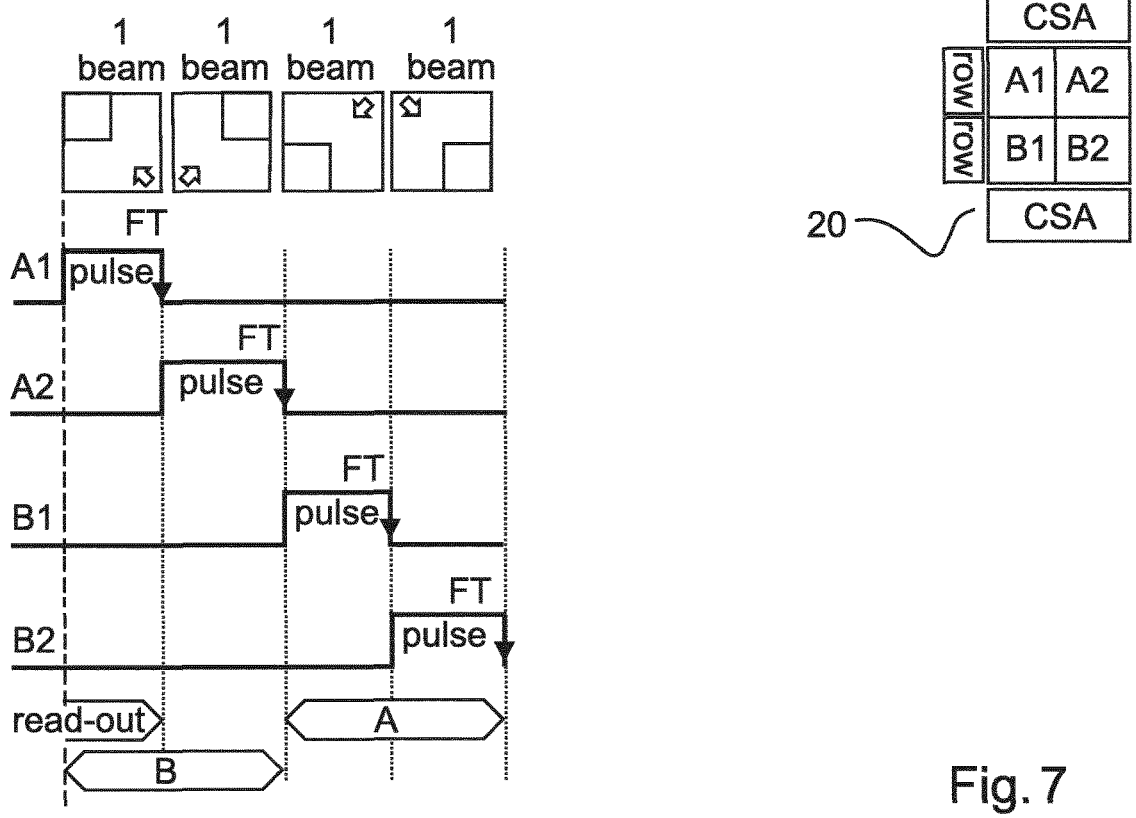
FIG. 7 shows a schematic diagram, and associated timing diagram, of a detector for imaging an object.

FIG. 7 shows an example of a detector with quad block frame transfer, with four beams passing through the object. After each illumination phase, frame transfer is applied. This means that the first part A1 of detector area A can be illuminated following which a second part A2 of detector area A can be illuminated with detector area A then being read out. During read out of detector area A, the first part B1 of detector area B can be illuminated following which a second part B2 of detector area B can be illuminated with detector area B then being read out. In this manner, the cycle time of such a detector is two times the read out time of a panel ($2t_{panel}$). Partitioning the frame transfer also into blocks of columns gives extra flexibility. For example, the exposures of A1 and A2 can be separated in the order to reduce or even avoid cross scatter, while they can still be read out together. Dual block frame transfer works most efficiently if the upper and lower panels of the detector are exposed alternatively. Quad block frame transfer gives extra flexibility, enabling additional efficient exposure schemes. Using split rows can give even more flexibility, and facilitates a method of having partitioned readout. This can also be done with a more general pixel addressing method. In an example, the detector of FIG. 7 has split rows (this is shown for the detector shown in FIG. 9, where for FIG. 9 to reach the areas in the middle (A2, A3, A6, etc) multiple rows in the same rows are needed). In this manner, area A1 can be read out separately to Area A2, and area B1 read out separately to area B2. This means that area A1 could be read out and area A2 could be readout during that irradiation. The cycle time for this detector is equal to the read out time of a panel ($t_{panel}$). A reset could be applied after irradiation of area A1 and then area A2, with this either being global and "cleaning" the detector ready for irradiation or local, and make area B ready for illumination. In this way, the system architecture is kept simple. Or, after irradiation of area A1 and after frame transfer, a reset can be applied. This could again be a global reset, or be applied to area A2, that is to be irradiated next or other areas as required.

Figure 8:
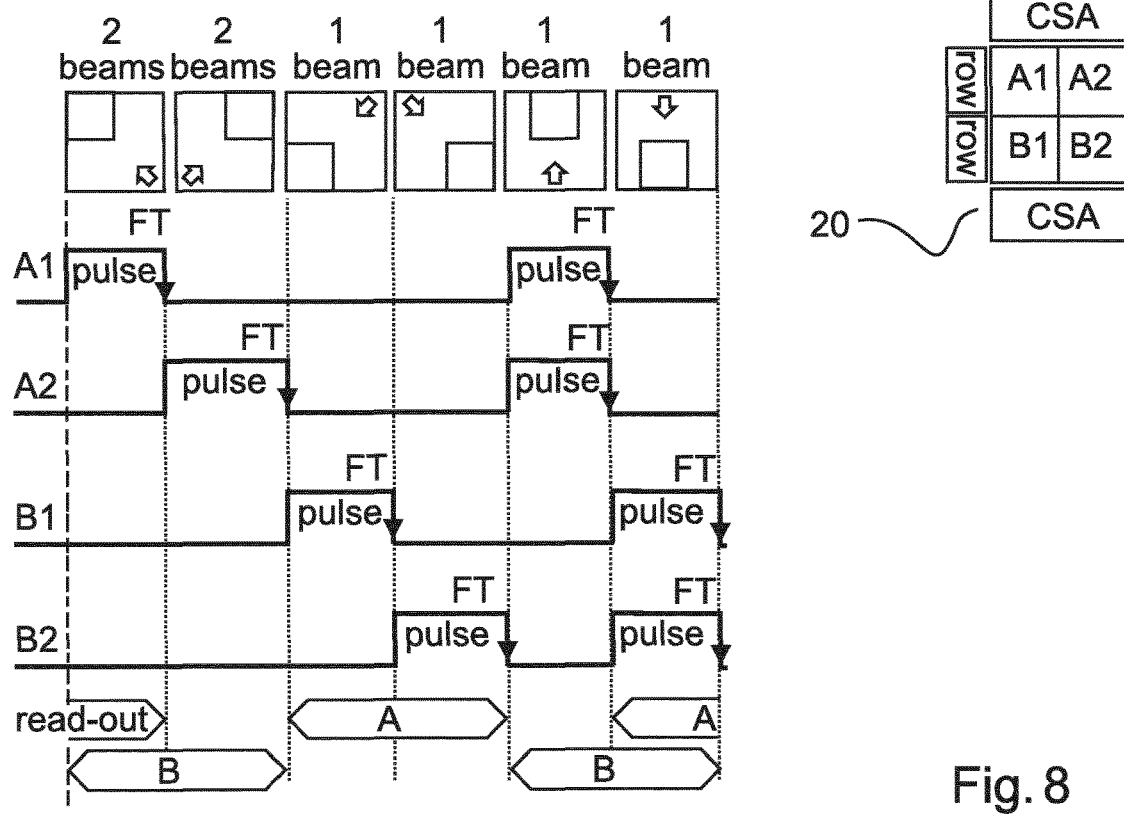
FIG. 8 shows a schematic diagram, and associated timing diagram, of a detector for imaging an object.

FIG. 8 shows an example of a detector with quad block frame transfer, with six beams passing through the object. After each illumination phase, frame transfer is applied. This means that the first part A1 of detector area A can be illuminated following which a second part A2 of detector area A can be illuminated with detector area A then being read out. During read out of detector area A, the first part B1 of detector area B can be illuminated following which a second part B2 of detector area B can be illuminated with detector area B then being read out. An area comprising a portion of both area A1 and A2 can then be illuminated with frame transfer being applied to both areas, following which area A is read out. During read out an area comprising a portion of both area B1 and B2 can then be illuminated with frame transfer being applied to both areas, following which area B is read out. In this manner, the cycle time of such a detector is three times the read out time of a panel ($3t_{panel}$). Reset can operate as discussed above.

Figure 9:
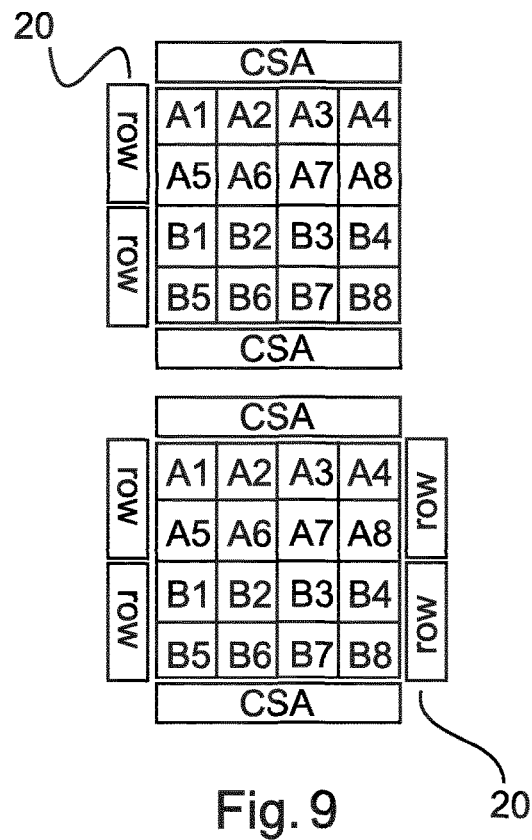
FIG. 9 shows a schematic diagram, and associated timing diagram, of a detector for imaging an object.

FIG. 9 shows an example of a detector with n×m block frame transfer, with the particular example shown in FIG. 9 having 8 areas of area A and 8 areas of area B; other numbers of areas are possible. Operation of the detector is as described above with reference to FIGS. 5-8. A typical switching scheme is:

Expose one or more partitions of panel half A.

Exposures can be subsequently, to avoid cross scatter, or simultaneously, to reduce motion artifacts.

As soon as a frame transfer block (partition) has been exposed, a signal charge can be safely stored in the sample and hold.

The pulses can be very close to each other "back to back".

Readout of panel half A

The same can then be applied for panel half B

The bottom half of FIG. 9 shows a detector with split rows, such that the detector area A has more than one frame transfer. Using split rows giving even more flexibility.

SUMMARY

The described apparatus and detector is directed toward imaging applications, such as 4D imaging. This means a 3D patient volume is acquired and displayed in real time (the fourth dimension). Here, because it takes time to reconstruct the 3D volume, "real time" in this sense means "semi real time", but the user has the impression that real rime operation is provided. To create a 3D volume several exposures from different angles are needed to reconstruct the volume. The time needed to acquire the views for 1 volume is too large with current flat X-ray detectors causing motion artifacts in the volume. Furthermore, the volume update rate (comparable to framerate in a movie) is too low to get sufficient live feedback for the procedure. In order to decrease the acquisition time needed several X-ray sources can be used that fire shortly after each other. It is also possible that several (or all) X-ray sources fire at the same time to decrease the acquisition time even further, in this case cross scatter will become an issue. It is to be noted that all these sources do not only allow 4D imaging but also tomographic imaging or conventional 2D imaging from several fixed angles.

On the X-ray detection side several detectors are needed to acquire the radiation of all the X-ray sources. In practice this means that multiple detectors are needed that will make the system unrealistically expensive, but also patient access will be limited. To address this, the apparatus and detector described here, in essence provides one large flat x-ray detector that can mimic the functionality of several individual detectors.

Current flat X-ray detectors need time to readout the exposed image. During this time other parts of the detector cannot be irradiates, because the image content will be changed. However, by providing the detector with a storage memory the image can be transferred after the irradiation to the memory part of the detector. The detector can than immediately accept the next irradiation pulse, without disturbing the previous image content. This functionality is called "frame transfer". The storage node can be physically placed in the pixel but also on a dedicated part of the flat x-ray detector.

The detector has several functionality states, including having readout storage node(s):

Accept, and in some cases integrate, irradiation on the sensor elements (photo diode, direct conversion material, photon counting pixels and detectors, etc.)

Move image content from sensor element to storage node

Reset the sensor element (this can be combined with point 2)

To make the detector internal control easier, the above three functionalities can be controlled for groups of pixels. So with one command the image content is moved to the storage node for all the pixels in that group (or resetted). Size and shape of a group can be defined either by hardwiring in the flat panel itself or by allocating group addresses to each pixel (different addresses can be programmed on the fly). It is also possible that groups overlap, the overlapping area will then be controlled by the commands from both groups. Examples of the grouping of pixels are shown below in FIG. 10.

Further Applications

Frame transfer provides equal time window in the image during continuous irradiation.

Figure 10:
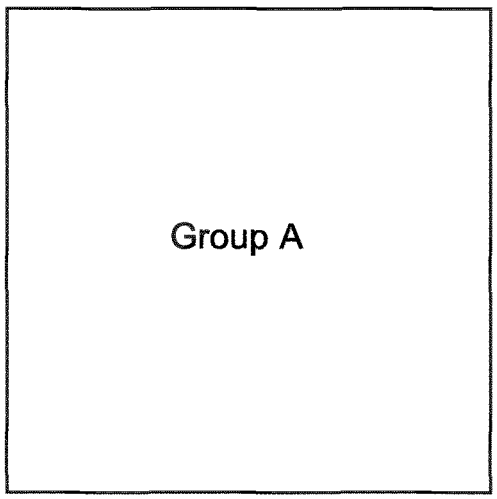
FIG. 10 shows a schematic example, of group allocations for detectors used for imaging an object.
Figure 10:
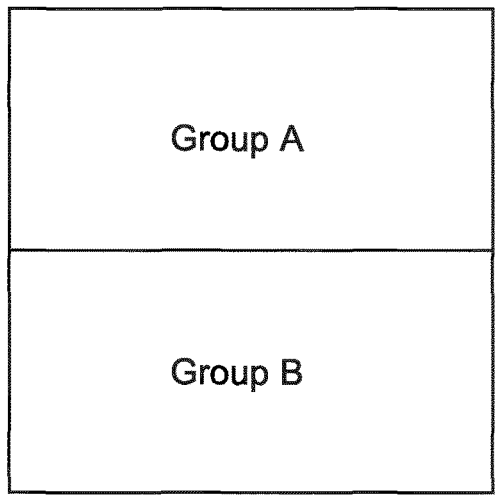
Figure 10:
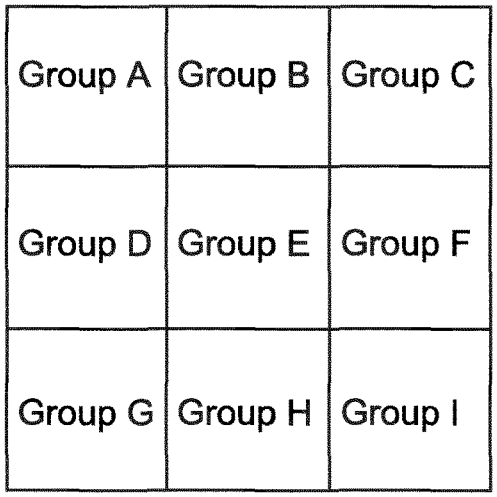
Figure 10:
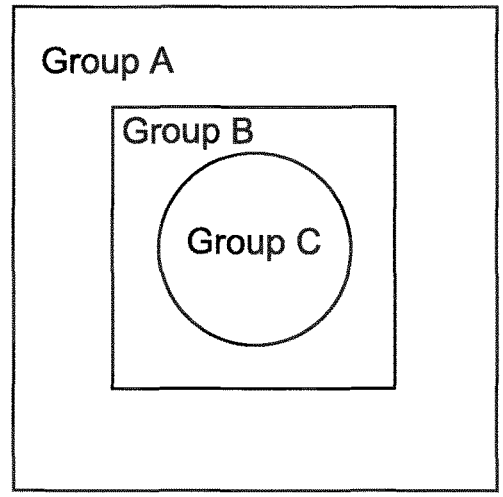
Figure 10:
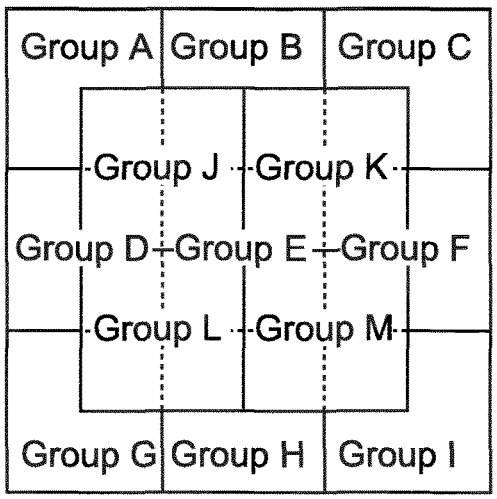
Figure 10:
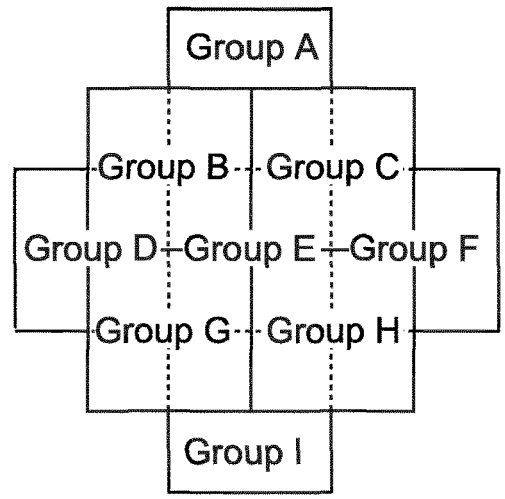

Frame transfer allows higher framerates during monoplane and biplane applications Frame transfer allows back to back irradiations during biplane acquisitions. FIG. 10 shows examples of group allocations of pixels. Groups of pixels can be overlapping if designed as shown in FIG. 10. What this means, for example, is that group A controls the complete detector area, Group B the small square in the middle and group C only the circle. The groups can be designed to be smaller, so the readout is faster. For instance for "nine groups", the areas can be made smaller for faster readout and overlap one large group that covers the complete detector area.

Figure 11:
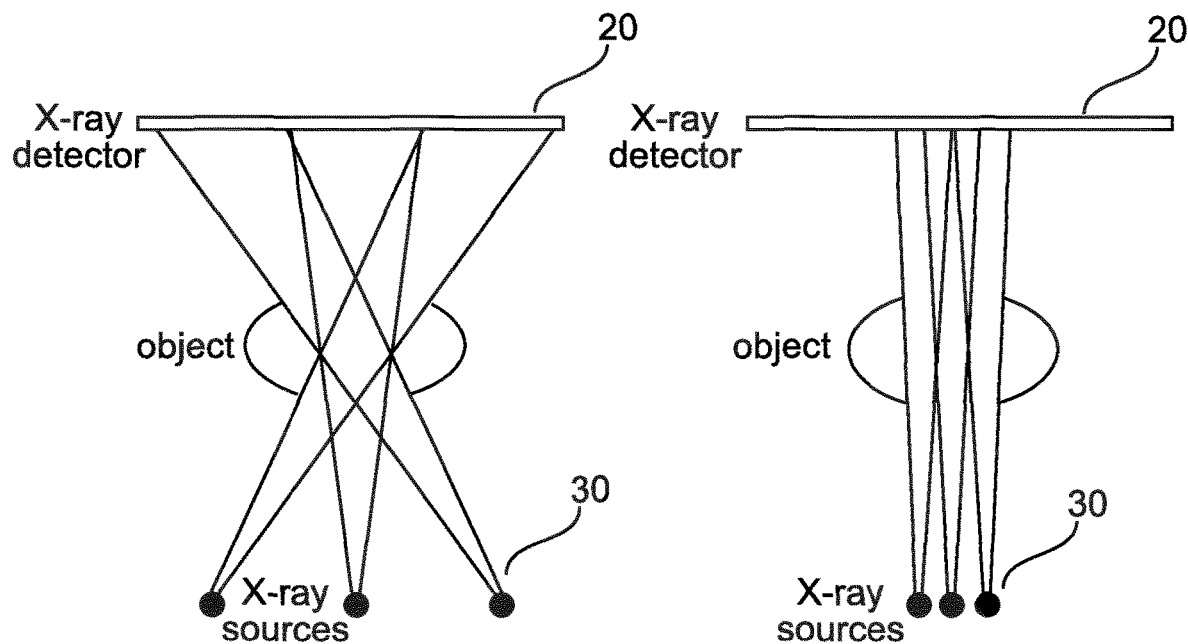
FIG. 11 shows schematic representations of X-ray beams passing through an object of an apparatus for imaging the object.
Figure 12:
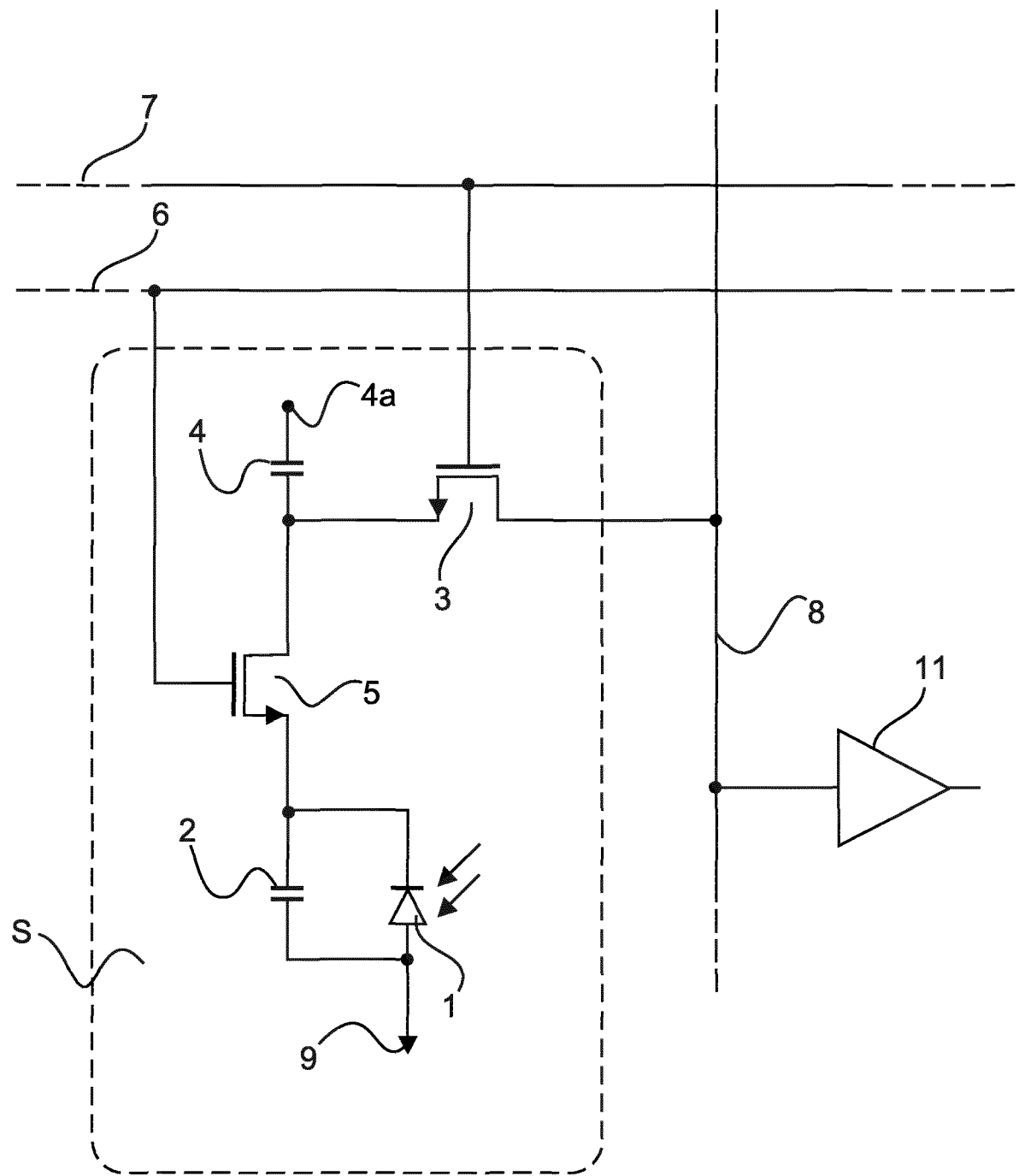
FIG. 12 shows a circuit schematic diagram of a partial arrangement of an example of the frame transfer functionality relating to one part of a detector for imaging an object.

FIG. 11 shows representative geometries of apparatuses that can be used for imaging an object, such as for 4D imaging. In the apparatus shown on the left-hand side of FIG. 11 three x-ray sources 30 are shown spaced apart with their respective x-ray beams passing through the object and being incident on respective separate areas of the detector 20. In this manner beams can cross each other to give information for 3-D reconstruction. In the apparatus shown in the right-hand side of FIG. 11 some x-ray beams can also be parallel, for example the central beam in the apparatus shown in the left-hand side of FIG. 11 can be divided into three beams. In this way, the same field of view (FOV) using several sources with small anode angle can be reached or achieved as the FOV of one source with a large anode angle. An advantage of this is that there is reduced scatter, and a smaller spot size. It is to be noted, that the exposure of the central beam shown in the right-hand side of FIG. 11 is in a subsequent cycle of the corresponding panel half (because of beam overlap on detector). FIG. 12 is used to explain how frame transfer can be applied to a detector to be used in imaging an object, such as 4D imaging. Frame transfer can be described as follows: The collected signal in the pixel must be readout or stored before any other operation (like reset or new signal collection) destroys the signal. When the readout phase takes a relatively long time it can be beneficial to store the pixel signal on a storage node in the pixel. Storing the pixel signal on a storage node is normally done with a so called sample & hold circuit. When the copy process is completed the original signal can be destroyed. One can also transfer the pixel signal (charge) to a storage capacitor (as is done on capacitor 4 of FIG. 12, as is now discussed in more detail.

FIG. 12 shows only one radiation-sensitive sensor S (pixel of the detector or detector matrix), provided with n-channel field effect transistors, with such a sensor also described in U.S. Pat. No. 6,894,283. Field effect transistors having a different construction can also be used in the context of the invention. A detector consists in known manner of a multitude of, for example 2000×2000 sensors S which are arranged in rows and columns. As discussed above, partitioned frame transfer is applied to the detector however with respect to FIG. 12, frame transfer as applied to a partitioned part of the detector (for example area A or area B is being described). The respective first sensors S of a row of the detector matrix together form the first column whereas the respective second sensors of each row together constitute the second column, etc. Each sensor S includes a photosensor element. When suitable semiconductors are used, the photosensor element itself may already be sensitive to X-rays. However, it may also be a light-sensitive photodiode 1 which receives light whenever X-rays are incident on a scintillator layer arranged on or above it. In the absence of a scintillator layer the arrangement is also suitable for the direct detection of light. Parallel to the terminals of the photodiode 1 there is connected a storage capacitor 2. The anode of the photodiode 1 and an electrode of the storage capacitor 2 are connected to a common electrode 9 which biases it with a negative DC voltage. The cathode of the photodiode 1 and the other electrode of the storage capacitor 2 are connected to a source terminal of a control field effect transistor 5. The drain terminal of the control field effect transistor 5 in its turn is connected to a source terminal of a switching field effect transistor 3. When radiation is incident on the photodiode 1, charge carrier pairs (charges) are generated in the photodiode 1, with the result that the charged storage capacitor is partly discharged. The discharge is dependent on the number of photons incident on the photodiode 1. Each sensor can be individually read out by compensating the respective charge deficiency via the conductive channels of the field effect transistors 3, 5. To this end, a control line 6 and a switching line 7 are provided for each row of the partitioned part of the sensor detector matrix. The switching line 7 is connected to the gate terminals of the switching field effect transistors 3 and the control line is connected to the gate terminals of the control field effect transistors 5 of the sensors S. The switching and control lines 6, 7 thus activate the field effect transistors 3, of the associated row of the detector. They are driven, for example by means of a suitable driver circuit applying different analog control voltages to the lines 6, 7. The driver circuit serves to activate the rows of the sensor partitioned detector successively in order to read out the charges stored in the sensors S of that partitioned part. A read-out line 8 is provided for each column of the detector matrix. All read-out lines 8 are connected to the drain terminals of the switching field effect transistors 3 of the sensors of the relevant column. An amplifier 11 is associated with each read-out line 8, the amplifier integrating the charges row-wise flowing in the individual sensors S. The amplifiers 11 are preceded by an analog multiplexer (not shown) whose inputs are connected to the outputs of the amplifiers. The analog multiplexer converts the charges, arriving simultaneously and in parallel from each time one row of the detector matrix, into a serial signal which is presented on a serial output of the analog multiplexer so as to be processed further. An electrode of a further capacitor 4 is connected to the drain terminal of the control field effect transistor 5 and the source terminal of the switching field effect transistor 3, respectively, the other electrode 4a of said further capacitor also being connected to the general electrode 9 or a general electrode which is independent therefrom. It is possible to insert one or more cascode transistors in the connection between the control field effect transistor 5 and the switching field effect transistor 3 of each sensor S in order to stabilize the drain voltage across the control field effect transistor 5.

In another exemplary embodiment, a computer program or computer program element is provided that is characterized by being configured to execute the method steps of the method according to one of the preceding embodiments, an appropriate system. The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for imaging an object, comprising:
an X-ray detector;
at least one X-ray source;
wherein the at least one X-ray source is configured to be positioned relative to the X-ray detector such that at least a part of the region between the at least one X-ray source and the X-ray detector is an examination region for accommodating an object;
wherein the X-ray detector comprises a plurality of X-ray detecting areas, the plurality of X-ray detecting areas comprising a first area comprising a plurality of first pixels and a second area comprising a plurality of second pixels;
wherein a first radiation emitted by the at least one X-ray source is received by at least a portion of the first pixels, and a second radiation emitted by the at least one X-ray source is received by at least a portion of the second pixels, and the first radiation is a pulse of radiation and the second radiation is another pulse of radiation that is different than the first radiation, wherein the X-ray detector is configured such that the X-ray radiation received by a pixel leads to the generation of signal in that pixel;
wherein the X-ray detector comprises at least one first plurality of storage nodes associated with the first area and at least one second plurality of storage nodes associated with the second area, wherein the at least one first plurality of storage nodes is configured to store a plurality of first signals representative of corresponding signals on the plurality of first pixels and the at least one second plurality of storage nodes is configured to store a plurality of second signals representative of corresponding signals on the plurality of second pixels;
wherein the at least one second plurality of storage nodes is configured to store the plurality of second signals after the at least one first plurality of storage nodes is configured to store the plurality of first signals; and
wherein the X-ray detector comprises at least one reset, the at least one reset configured to reset the plurality of first pixels and configured to reset the plurality of second pixels, wherein the X-ray detector is configured such that the first radiation emitted by the at least one X-ray source is received by the portion of first pixels before the at least one reset resets the plurality of second pixels and the detector is configured such that the at least one reset resets the plurality of second pixels before the second radiation emitted by the at least one X-ray source is received by the portion of second pixels.

2. The apparatus according to claim 1, wherein, the X-ray detector comprises at least one first read out associated with the at least one first plurality of storage nodes and at least one second read out associated with the at least one second plurality of storage nodes, wherein the at least one first read out is configured to read out the plurality of first signals and the at least one second read out is configured to read out the plurality of second signals, wherein the X-ray detector is configured such that the second radiation emitted by the at least one X-ray source is received by the portion of second pixels before read out of the plurality of the first signals is finished.

3. The apparatus according to claim 1, wherein the X-ray detector is configured such that the second radiation emitted by the at least one X-ray source is received by the portion of second pixels before the at least one reset resets the plurality of first pixels, and the X-ray detector is configured such that the at least one reset resets the plurality of first pixels before a third radiation emitted by the at least one X-ray source is received by the portion of first pixels.

4. The apparatus according to claim 3, wherein the X-ray detector is configured such that the third radiation emitted by the at least one X-ray source is received by the portion of first pixels before read out of the plurality of the second signals is finished.

5. An X-ray detector for imaging an object, wherein, the X-ray detector comprises a plurality of X-ray detecting areas, the plurality of X-ray detecting areas comprising a first area comprising a plurality of first pixels and a second area comprising a plurality of second pixels;
wherein first radiation emitted by at least one X-ray source is received by at least a portion of the first pixels, and second radiation emitted by the at least one X-ray source is received by at least a portion of the second pixels, and the first radiation is a pulse of radiation and the second radiation is another pulse of radiation that is different than the first radiation, wherein the X-ray detector is configured such that the X-ray radiation received by a pixel leads to the generation of signal in that pixel;
wherein the X-ray detector comprises at least one first plurality of storage nodes associated with the first area and at least one second plurality of storage nodes associated with the second area, wherein the at least one first plurality of storage nodes is configured to store a plurality of first signals representative of corresponding signals on the plurality of first pixels and the at least one second plurality of storage nodes is configured to store a plurality of second signals representative of corresponding signals on the plurality of second pixels;
wherein, the at least one second plurality of storage nodes is configured to store the plurality of second signals after the at least one first plurality of storage nodes is configured to store the plurality of first signals; and
wherein the X-ray detector comprises at least one reset, the at least one reset configured to reset the plurality of first pixels and configured to reset the plurality of second pixels, wherein the X-ray detector is configured such that the first radiation emitted by the at least one X-ray source is receivable by the portion of first pixels before the at least one reset resets the plurality of second pixels and the detector is configured such that the at least one reset resets the plurality of second pixels before the second radiation emitted by the at least one X-ray source is receivable by the portion of second pixels.

6. A method for imaging an object, comprising:
receiving by at least a portion of first pixels of a first area of an X-ray detector first radiation emitted by at least one X-ray source, and the first radiation is a pulse of radiation, wherein the X-ray detector is configured such that X-ray radiation received by a pixel leads to the generation of signal in that pixel;
storing, in at least one first plurality of storage nodes associated with the first area, a plurality of first signals representative of corresponding signals on the plurality of first pixels;
resetting the plurality of second pixels;
receiving by at least a portion of second pixels of a second area of the X-ray detector second radiation emitted by the at least one X-ray source, and the second radiation is a pulse of radiation that is different than the first radiation; and storing, in at least one second plurality of storage nodes associated with the second area, a plurality of second signals representative of corresponding signals on the plurality of second pixels.

7. The method according to claim 6, further comprising:
reading out by at least one first read out associated with the at least one first plurality of storage nodes the plurality of first signals.

8. The method according to claim 5, further comprising:
resetting the plurality of first pixels; and
receiving by the portion of first pixels of the first area of the X-ray detector a third radiation emitted by the at least one X-ray source.

9. The method according to claim 8, further comprising:
reading out by at least one second read out associated with the at least one second plurality of storage nodes the plurality of second signals.

10. The method according to claim 6, further comprising:
receiving by a first sub-portion of first pixels of the first area of the X-ray detector radiation emitted by an X-ray source; and
receiving by a second sub-portion of first pixels of the first area of the X-ray detector another radiation emitted by an X-ray source different than the radiation; and
wherein the at least one first plurality of storage nodes comprises at least two plurality of storage nodes, and
storing, in a first plurality of storage nodes associated with the first area, a plurality of first signals representative of corresponding signals on the first sub-portion of first pixels;
storing, in a second plurality of storage nodes associated with the first area, a plurality of first signals representative of corresponding signals on the second sub-portion of first pixels, wherein the first plurality of storage nodes is different than the second plurality of storage nodes;
resetting the plurality of first pixels, and then resetting the plurality of second pixels;
receiving by a first sub-portion of second pixels of the second area of the X-ray detector radiation emitted by an X-ray source (B1); and
e2) receiving (154) by a second sub-portion of second pixels of the second area of the X-ray detector radiation emitted by an X-ray source; and
wherein the at least one second plurality of storage nodes comprises at least two plurality of storage nodes,
storing, in a first plurality of storage nodes associated with the second area, a plurality of second signals representative of corresponding signals on the first sub-portion of second pixels; and
storing, in a second plurality of storage nodes associated with the second area, a plurality of second signals representative of corresponding signals on the second sub-portion of second pixels, wherein the first plurality of storage nodes is different than the second plurality of storage nodes.

11. A non-transitory computer readable medium having one or more executable instructions stored thereon, which when executed by a processor, cause the processor to perform a method for imaging an object, the method comprising:
receiving by at least a portion of first pixels of a first area of an X-ray detector first radiation emitted by at least one X-ray source, and the first radiation is a pulse of radiation, wherein the X-ray detector is configured such that X-ray radiation received by a pixel leads to the generation of signal in that pixel;
storing, in at least one first plurality of storage nodes associated with the first area, a plurality of first signals representative of corresponding signals on the plurality of first pixels;
resetting the plurality of second pixels;
receiving by at least a portion of second pixels of a second area of the X-ray detector second radiation emitted by the at least one X-ray source, and the second radiation is a pulse of radiation that is different than the first radiation; and
storing, in at least one second plurality of storage nodes associated with the second area, a plurality of second signals representative of corresponding signals on the plurality of second pixels.

* * * * *